(12) United States Patent
LeBeau et al.

(10) Patent No.: US 9,549,769 B2
(45) Date of Patent: Jan. 24, 2017

(54) FLEXIBLE DEPTH PROBE

(71) Applicant: Smith & Nephew, Inc., Memphis, TN (US)

(72) Inventors: Jason Roch LeBeau, Bridgewater, MA (US); Carmel Ilka Bijoux, Boston, MA (US); Steven Mark Bowman, Sherborn, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/246,300

(22) Filed: Apr. 7, 2014

(65) Prior Publication Data
US 2014/0222010 A1 Aug. 7, 2014

Related U.S. Application Data

(63) Continuation of application No. 13/234,636, filed on Sep. 16, 2011, now Pat. No. 8,728,088.

(51) Int. Cl.
| *A61B 17/58* | (2006.01) |
| --- | --- |
| *A61B 17/60* | (2006.01) |
| *A61F 2/00* | (2006.01) |
| *A61B 17/88* | (2006.01) |
| *A61B 17/17* | (2006.01) |
| *A61B 17/00* | (2006.01) |

(52) U.S. Cl.
CPC .............. *A61B 17/88* (2013.01); *A61B 90/06* (2016.02); *A61B 17/1714* (2013.01); *A61B 2017/00455* (2013.01); *A61B 2090/062* (2016.02)

(58) Field of Classification Search
CPC . A61B 19/46; A61B 2019/461; A61B 5/1072; A61B 17/1714; A61B 2017/00455; A61F 2/4657; A61F 2002/4662; A61F 2/4684; A61F 2/0805

USPC .. 606/102, 79, 80, 86 R, 138, 139, 144, 148
See application file for complete search history.

(56) References Cited

U.S. PATENT DOCUMENTS

| 4,779,349 | A | | 10/1988 | Odensten et al. | |
| --- | --- | --- | --- | --- | --- |
| 5,013,318 | A | * | 5/1991 | Spranza, III | A61B 5/1076 33/512 |
| 5,306,301 | A | | 4/1994 | Graf et al. | |
| 6,156,056 | A | * | 12/2000 | Kearns | A61B 17/0469 606/232 |
| 6,729,037 | B2 | | 5/2004 | White | |
| 6,729,307 | B2 | | 5/2004 | Dong | |

(Continued)

OTHER PUBLICATIONS

Silver, A.G., et al., "Comparison between Rigid and Flexible Systems for Drilling the Femoral Tunnel through an 1 Anteromedial Portal in Anterior Cruciate Ligament Reconstruction," Arthroscopy: The Journal of Arthroscopic and Related Surgery, vol. 26, Issue 6, pp. 790-795, Jun. 2010.
Andrews, James R., "ACL Reconstruction: Bone-Tendon-Bone Surgical Protocol," from "ToggleLoc Fixation Device with Zip Loop Technology," Biomet Sports Medicine, Mar. 2009, 12 pages.
"Game Plan: Strategies to Help Surgeons Get Patients Back in the Game" Fall 2009, vol. 2, No. 1, Biomet Sports Medicine, 4 pages.

(Continued)

*Primary Examiner* — Kevin T Truong
*Assistant Examiner* — Si Ming Ku
(74) *Attorney, Agent, or Firm* — Burns & Levinson LLP; Joseph M. Maraia

(57) ABSTRACT

An instrument includes a flexible shaft portion and a hook portion. The flexible shaft portion has a proximal end and a distal end and includes markings along an outer surface of the shaft portion. The hook portion is located at the distal end of the shaft portion. The shaft portion and the hook portion define a lumen that terminates in an opening at the hook portion.

25 Claims, 9 Drawing Sheets

(56) References Cited

U.S. PATENT DOCUMENTS

| | | | |
|---|---|---|---|
| 7,299,561 | B2 | 11/2007 | Castaneda |
| 7,485,119 | B2 | 2/2009 | Thelen et al. |
| 7,559,150 | B2* | 7/2009 | Fernandez ............. A61B 5/103 33/512 |
| 2002/0143234 | A1* | 10/2002 | LoVuolo .......... A61B 17/06109 600/30 |
| 2009/0049705 | A1 | 2/2009 | Kim |
| 2009/0151181 | A1 | 6/2009 | Kim et al. |
| 2009/0272001 | A1 | 11/2009 | Dell Oca |
| 2011/0208194 | A1* | 8/2011 | Steiner ............... A61B 17/1631 606/80 |
| 2012/0053641 | A1 | 3/2012 | Meridew |
| 2012/0221007 | A1* | 8/2012 | Batten et al. ................... 606/80 |

OTHER PUBLICATIONS

"Anatomic ACL Reconstruction Using the Clancy Anatomic Cruciate Guide/Flexible Drill System," JointIntelligence, vol. 1, Issue 2, Nov. 2009, 5 pages.

"Symmetry Medical: Acetabular Screw Preparation System," brochure from Symmetry Medical Othy, 2005, 2 pages.

"Salvin Dental Specialties: Flexible Tip Implant Depth Gauge with Ergonon," reprinted from http://salvin.comfFlexible-Tip-Implant-Depth-Gauge-With-Ergonomic-Handle-pluD . . . on Jun. 22, 2011, 1 page.

"Bullseye Anatomic Cruciate Reconstruction System," brochure from ConMed Linvatec, 2009, 16 pages.

"VersiTomic Flexible Reaming System," brochure from Stryker, 2010, 6 pages.

\* cited by examiner

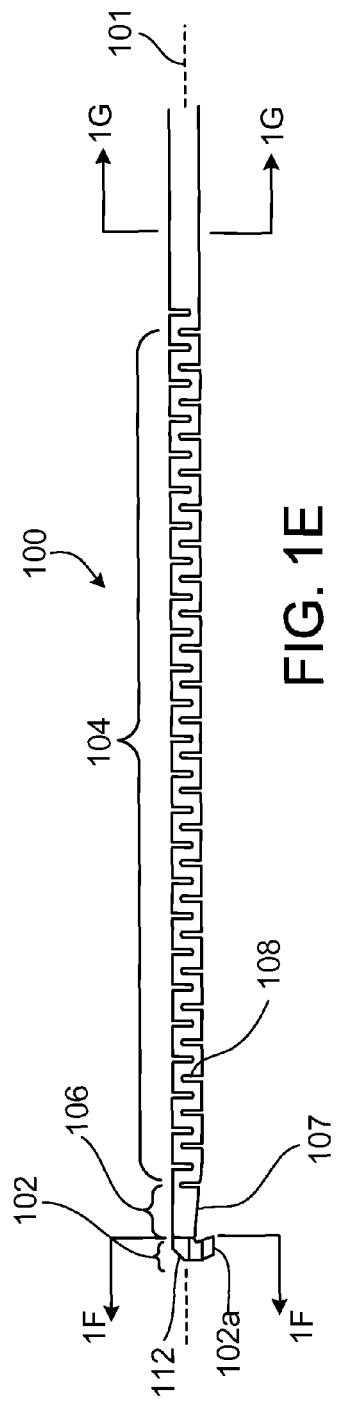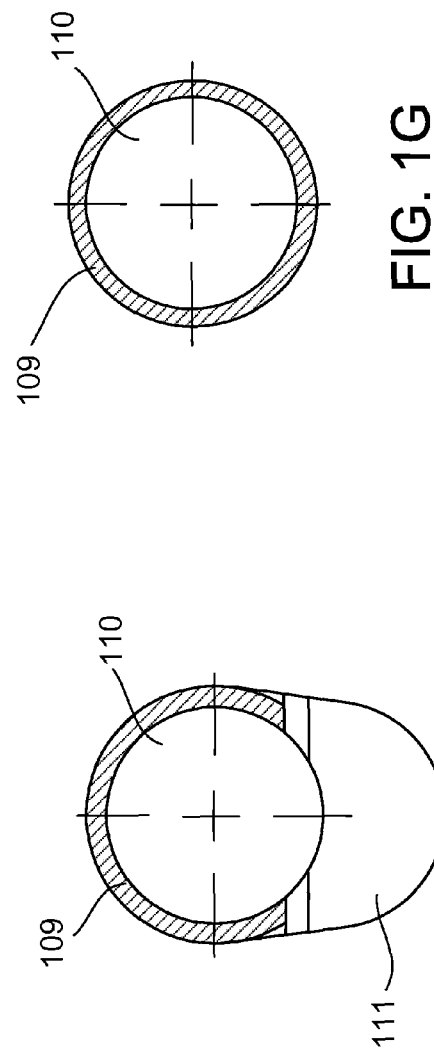

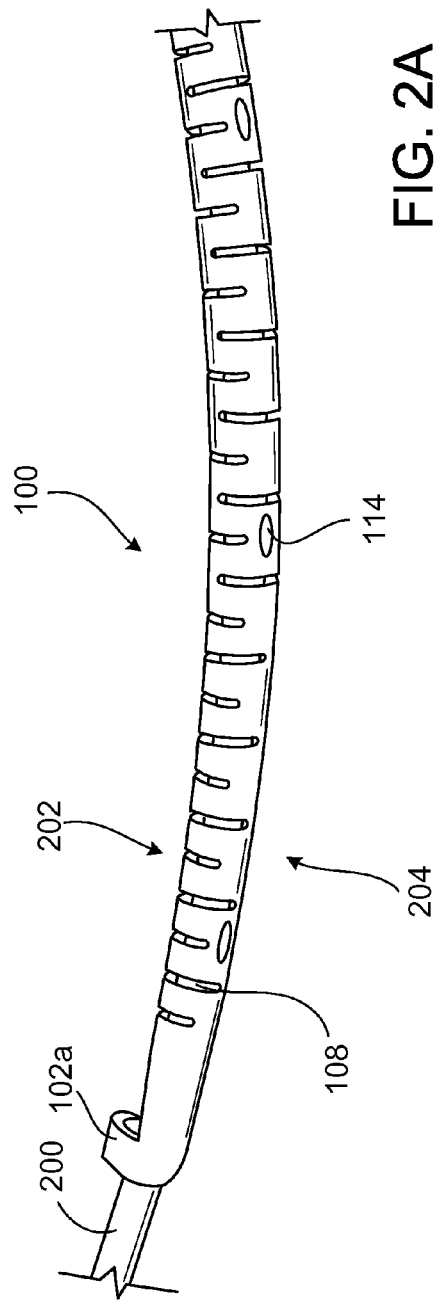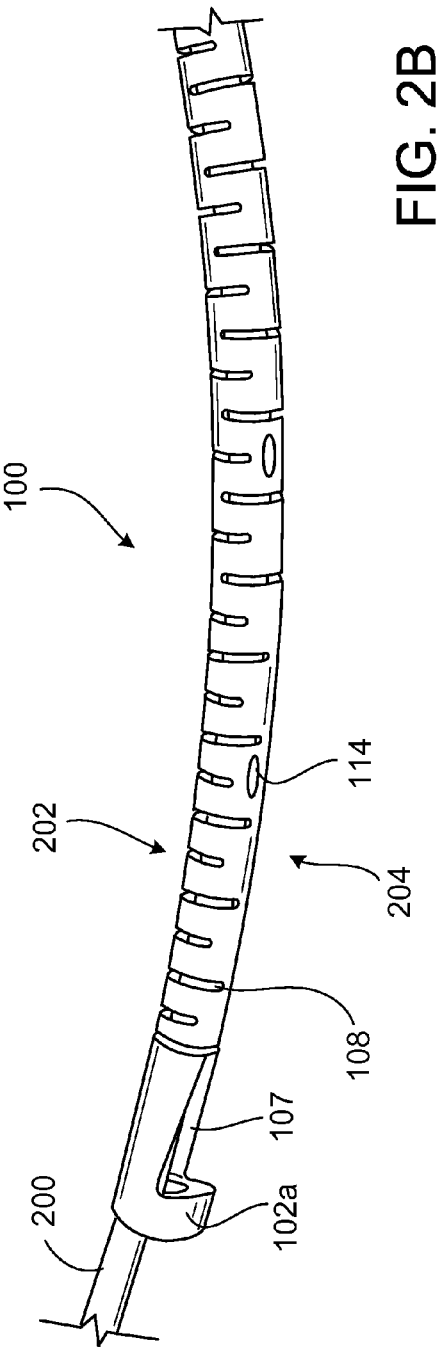

FLEXIBLE DEPTH PROBE

CROSS-REFERENCE TO RELATED APPLICATIONS

This application is a continuation of and claims priority to U.S. patent application Ser. No. 13/234,636, filed Sep. 16, 2011, entitled "FLEXIBLE DEPTH PROBE," the entire teachings of all of the above are incorporated herein by reference as though fully set forth herein.

TECHNICAL FIELD

This document relates to determining bone tunnel depth.

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials. The replacement tissue graft is implanted by securing one end of the tissue graft in a socket formed in a passage within the femur, and passing the other end of the graft through a passage formed in the tibia.

SUMMARY

According to one aspect, an instrument includes a flexible shaft portion and a hook portion. The flexible shaft portion has a proximal end and a distal end and includes markings along an outer surface of the shaft portion. The hook portion is located at the distal end of the shaft portion. The shaft portion and the hook portion define a lumen that terminates in an opening at the hook portion.

Implementations of this aspect may include one or more of the following features.

For example, the hook portion may include a tip. The tip may extend beyond an outer diameter of the flexible shaft portion. The hook portion may include a chamfer on a surface opposite the tip. The instrument may further include a chamfered connecting portion connecting the hook portion and the flexible shaft portion. The chamfered portion may also define the lumen. The hook portion may include a tip, and the chamfered connecting portion may include a chamfer along a tip-facing side of the chamfered portion. The shaft portion may include multiple, spaced apart voids along a length of the shaft portion. The voids may be configured to provide the shaft with flexibility. The voids may be configured to provide the shaft with flexibility sufficient to allow the shaft to flex at least 40 degrees without damage. The proximal end of the shaft may include an orientation indicator that indicates the orientation of the hook portion.

According to another aspect, a method of determining a length of a bone tunnel using an instrument includes placing the instrument onto a curved guide wire that passes through the bone tunnel, moving the instrument along the curved guide wire until a hook portion passes through a first opening of the bone tunnel, through the bone tunnel, and out a second opening of the bone tunnel, orienting the instrument such that a tip of the hook portion substantially faces an outer curvature of the guide wire, retracting the instrument until the hook portion engages a cortical surface of the bone, and determining the length of the bone tunnel based on markings along an outer surface of a flexible shaft portion. The instrument includes a flexible shaft portion and a hook portion at a distal end of the shaft.

Implementations of this aspect may include one or more of the following features.

For example, the shaft portion and the hook portion may define a lumen that terminates in an opening at the hook portion. Placing the instrument onto the curved guide wire may include threading the hole and lumen over the guide wire. The instrument may be oriented such that the tip of the hook portion substantially faces an inner curvature of the guide wire while the hook portion passes through the first opening of the bone tunnel, through the bone tunnel, and out the second opening of the bone tunnel. Orienting the instrument such that the tip of the hook portion substantially faces the outer curvature of the guide wire may include rotating the instrument around the guide wire until the tip of the hook portion substantially faces the outer curvature of the guide wire. The method of determining the length of a bone tunnel using the instrument may include disengaging the hook portion from the cortical surface, orienting the instrument such that the tip of the hook portion substantially faces an inner curvature of the guide wire, and moving the device along the curved guide wire until the hook portion passes through the second opening of the bone tunnel, through the bone tunnel, and out the first opening of the bone tunnel. The bone tunnel may be a femoral tunnel. The guide wire may be curved at least 40 degrees such that moving the instrument along the curved guide wire causes the flexible shaft to flex at least 40 degrees. The method of determining the length of a bone tunnel using the instrument may include determining an orientation of the hook portion based on an orientation indicator that indicates the orientation of the hook portion. The orientation indicator may be located at the proximal end of the shaft.

The details of one or more implementations are set forth in the accompanying drawings and the description below. Other features, aspects, and advantages will become apparent from the description, the drawings, and the claims.

BRIEF DESCRIPTION OF THE DRAWINGS

FIG. 1E is a side view of the flexible depth probe.

FIG. 1F is a cross-sectional view of the flexible depth probe of FIG. 1E taken along the line 1F-1F in the direction of the arrows.

FIG. 1G is a cross-sectional view of the flexible depth probe of FIG. 1E taken along the line 1G-1G in the direction of the arrows.

FIG. 2A is a side view of the flexible depth probe placed onto a guide wire with a tip of the hook portion facing an inner curvature of the guide wire.

FIG. 2B is a side view of the flexible depth probe placed onto a curved guide wire with a tip of the hook portion facing an outer curvature of the guide wire.

DETAILED DESCRIPTION

This document describes an example of a flexible depth probe for determining the depth or length of a bone tunnel. The flexible depth probe can, for example, be used to determine the length of a bone tunnel within a femur. In some implementations, the flexible depth probe can bend beyond 40 degrees, for example, to 42 degrees.

Figure 1A:
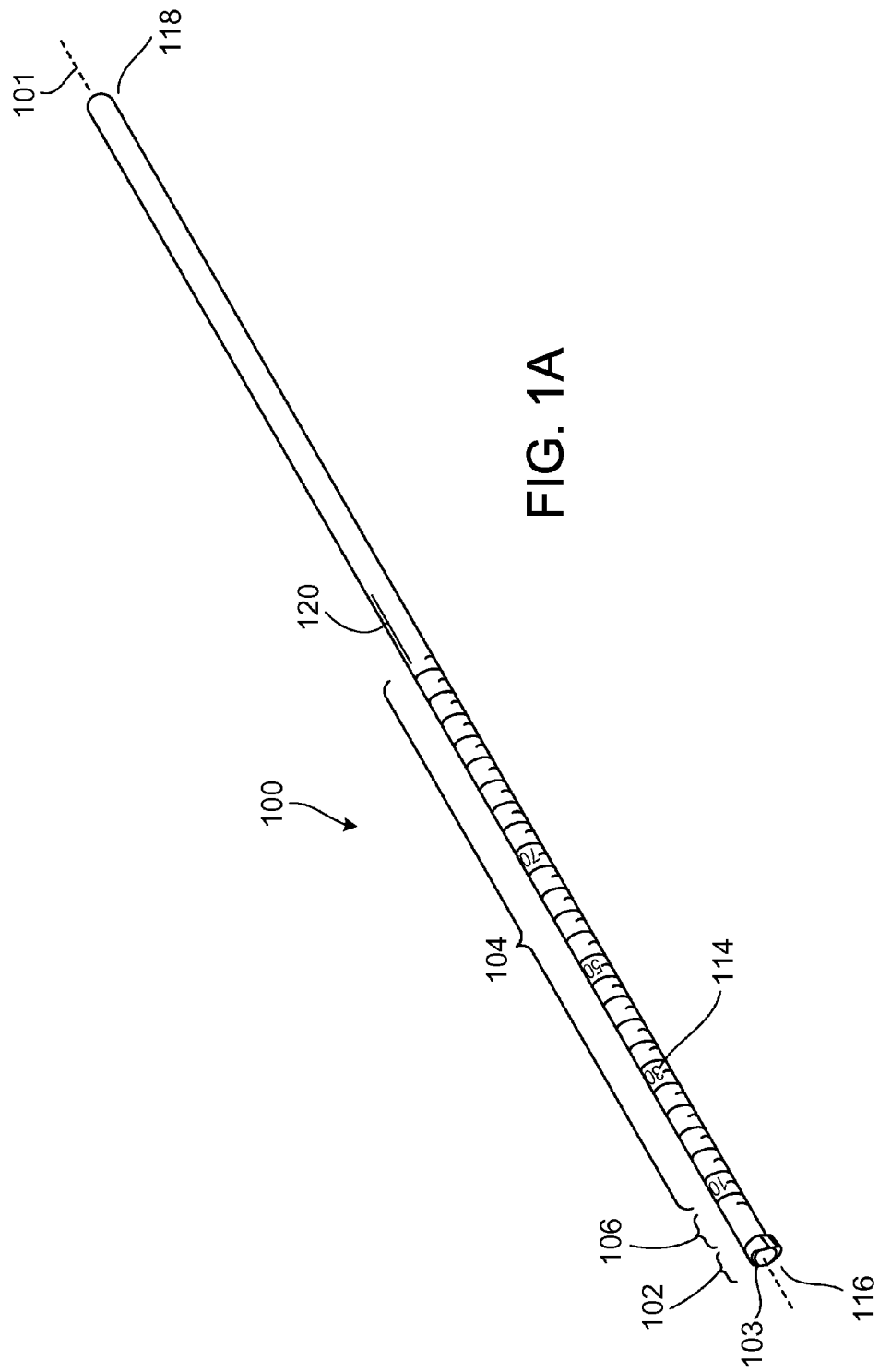
FIG. 1A is a perspective view of a flexible depth probe.
Figure 1B:
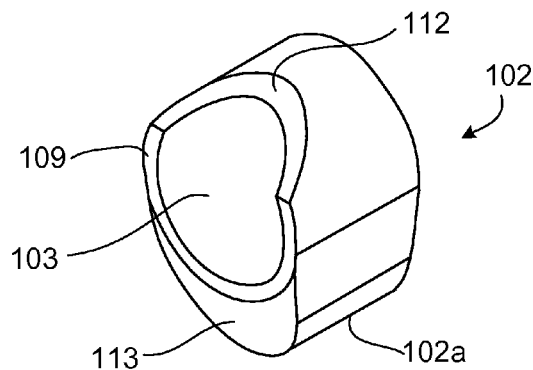
FIG. 1B is an enlarged perspective view of a hook portion of the flexible depth probe.
Figure 1C:
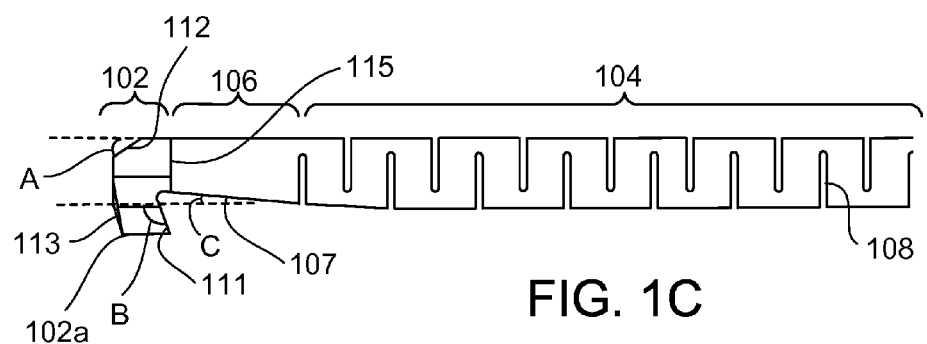
FIG. 1C is a partial side view of the flexible depth probe.
Figure 1D:
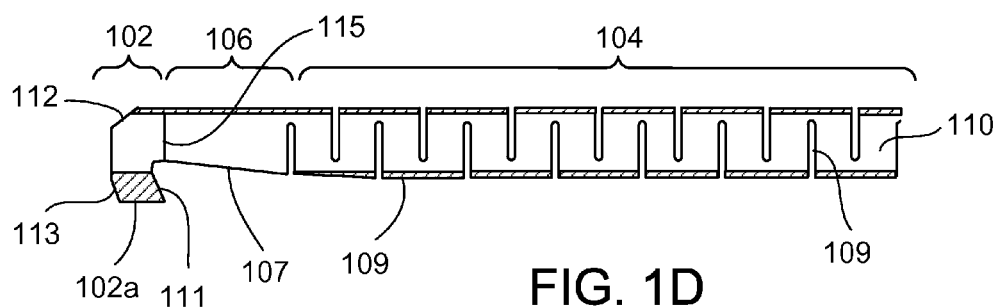
FIG. 1D is a cross-sectional view of the probe.

FIGS. 1A-1G illustrate an example of an implementation of a flexible depth probe 100. The probe 100 may be used as an instrument, for example, in determining the length of a bone tunnel in the femur, or femoral tunnel, during anterior cruciate ligament (ACL) surgery. The probe 100 includes a hook portion 102, a flexible shaft portion 104, and a chamfered connecting portion 106. Flexible depth probe 100 defines a lumen 110 that starts at the proximal end 118 and terminates in an opening 103 at the distal end 116 (as best seen in FIG. 1B). The overall length of the flexible depth probe 100 can be, for example, 30 cm. The diameter of the flexible shaft portion 104 can be 3 mm, and the diameter of lumen 110, which allows a guide wire to fit within it, can be 2.7 mm. The probe wall 109 surrounds the lumen 110 and can be 0.24 mm in wall thickness (as best seen in FIG. 1D). The flexible depth probe 100 can be made from various materials including, but not limited to, metals and alloys including titanium, stainless steel, anodized aluminum, and nickel titanium (nitinol), as well as different types of plastics and polymers. In some cases, the flexible depth probe 100 can be made from a combination of different materials.

The flexible shaft portion 104 of depth probe 100 includes multiple, spaced apart voids 108 configured to provide the shaft with flexibility, such that the flexible shaft portion 104 can bend beyond, for example, 40 degrees. The spaced apart voids 108 are in the form of slices cut into alternating sides of the flexible shaft portion 104. The slices can be 0.3 mm in width and can be spaced 2 mm apart from each other. The spaced apart voids 108 can alternatively, or additionally, be in the form of a continuous spiral cut, interlocking cut, puzzle cut, or other appropriate cut arrangement that provides the shaft with flexibility and can be formed, for example, through electric discharge machining (EDM) or laser cutting. Alternatively, or additionally, inherent flexibility of the material used in constructing the flexible shaft portion 104, for example nitinol, can provide flexibility to the section.

Hook portion 102 has a tip 102a configured to engage or latch onto a cortical surface of the bone and a chamfer 112, on the side opposite the tip 102a, configured to allow the depth probe 100 to slide smoothly inside, for example, a bone tunnel without damaging the tunnel wall. The chamfer 112 forms an angle A of, for example, 35 degrees, or more generally about 20 to about 85 degrees, with respect to the longitudinal axis 101 of the depth probe 100 and can be, for example, 4.4 mm in length when viewed from the side. A lower portion of the opening 103 includes a semi-cylindrical portion while the chamfer 112 defines an upper curved portion of the opening 103 (as best seen in FIG. 1B), the lower and upper portions of opening 103 defining a circular perimeter around longitudinal axis 101 when viewed axially from the distal end 116. Alternatively, or additionally, the opening 103 may be entirely cylindrical. The chamfer 112 may or may not expose the interior lumen 110. The chamfer 112 may be replaced with a radius in some cases.

The tip 102a is in the shape of an oblique semi-cylinder. The distal face 113 and the proximal face 111 of the semi-cylinder are angled towards the proximal end 118. The distal face 113 is angled to help the hook portion 102 slide into the bone tunnel. The proximal face 111 is angled to help the tip 102a more easily latch onto the cortical surface of the bone. Alternatively, or additionally, the tip 102a can be textured or include additional materials, such as rubber, to more easily engage the cortical surface. The tip 102a can further be in the shape of other geometric forms, such as spheres, prisms, and pyramids, that allow the tip 102a to latch onto the cortical surface of the bone. As shown in FIGS. 1C-1G, the outermost surface of the tip 102a extends beyond the outer surface of the flexible shaft portion 104, for example, by 6 mm, and the proximal face of tip 102a forms an angle B, for example, of 110 degrees with respect to the longitudinal axis 101.

The chamfered connecting portion 106 connects the hook portion 102 to the flexible shaft portion 104 and includes a chamfer 107 along the same side as the tip 102a. The chamfered connecting portion 106 is configured to provide a smooth transition between the interface region 115 and the outer surface of the flexible shaft portion 104. The chamfer 107 can from an angle C of about 1 to about 30 degrees with respect to the longitudinal axis 101 of the depth probe 100 and can be, for example, 15 mm in length. The chamfer 107 may expose the interior lumen 110. As described further below, the chamfer 107 can provide a more secure engagement of the hook portion 102 to the cortical surface of the bone.

The orientation indicator 120 located proximal to the flexible shaft portion 104 indicates the rotational orientation of the hook portion 102 around the longitudinal axis 101 and can be, for example, a straight line 20 mm in length running parallel to longitudinal axis 101 on the side of the flexible depth probe 100 opposite the tip 102a. Markings 114 are placed along the outer surface of the flexible depth probe 100 to indicate the length of the object, for example a bone tunnel, and can include a plurality of numerical as well as line markings. The numerical markings indicate the distance along the outer wall of the flexible shaft portion 104, on the side of the tip 102a and the chamfer 107, between the interface region 115 and the respective numerical marking. The numerical markings can be placed every 10 mm on the same and/or opposite side of 102a. The line markings can be placed every 2 mm and can run along the entire circumference of the probe 100 at each marking location. Alternatively, or additionally, the spaced apart voids 108 can serve as the line markings.

In another implementation, numerical markings can be located further proximally, by a known distance, on the flexible depth probe 100 in relation to their corresponding line markings such that the distance along the outer wall of flexible shaft portion 104 may be determined by observing the numerical markings that are located further down proximally. The orientation indicator 120 and markings 114 can be painted or engraved using a variety of techniques, for example laser etching.

FIGS. 2A-2B show side views of the flexible depth probe 100 placed onto a guide wire 200. The guide wire 200 is generally straight and can be bent, reversibly or irreversibly, to a desired curvature. The guide wire 200 can be made from any appropriate materials, such as, but not limited to, materials used in making the flexible depth probe 100. Additionally, the guide wire 200 can be an existing guide wire or passing pin of a flexible drill system, such as the Clancy Flexible System by Smith & Nephew.

The guide wire 200 slidably fits within the lumen 110 of the flexible depth probe 100, as best seen in FIGS. 2A-2B. The length of the guide wire 200 can be 34 cm, and its diameter can be 2.4 mm. As the flexible depth probe 100 is inserted or threaded over the guide wire 200, the flexibility of the flexible shaft portion 104 allows the shaft portion 104 to conform to the shape of guide wire 200. For example, if the guide wire 200 is curved at least 40 degrees, moving the flexible depth probe 100 along the curved guide wire 200 causes the flexible shaft portion 104 of the depth probe 100 to flex at least 40 degrees. FIG. 2A shows the flexible depth probe 100 slidably threaded over the guide wire 200 and oriented such that the tip 102a of the hook portion 102 faces an inner curvature 202 of the guide wire 200. As described further below, this rotational orientation of the flexible depth probe 100 can be used for insertion into, for example, a femoral tunnel. By rotating the proximal end 118 of the flexible depth probe 100 with respect to the guide wire 200, the entire flexible depth probe 100, including the hook portion 102, rotates in a corresponding manner around the guide wire 200. FIG. 2B shows the flexible depth probe 100 slidably threaded over the guide wire 200 and rotated around the guide wire 200 such that the tip 102a of the hook portion 102 faces an outer curvature 204 of the guide wire 200. As described further below, this rotational orientation of the flexible depth probe 100 can be used for engaging or latching onto, for example, the cortical surface of a bone.

Figure 3A:
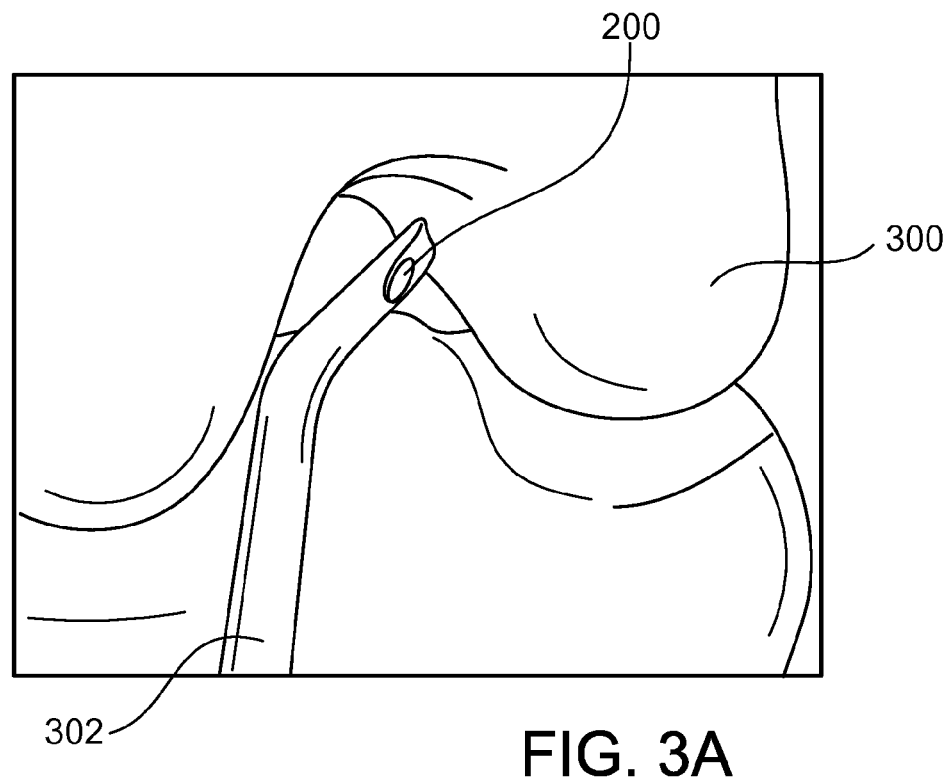
FIGS. 3A-3D illustrate a procedure for forming a femoral tunnel.
Figure 3B:
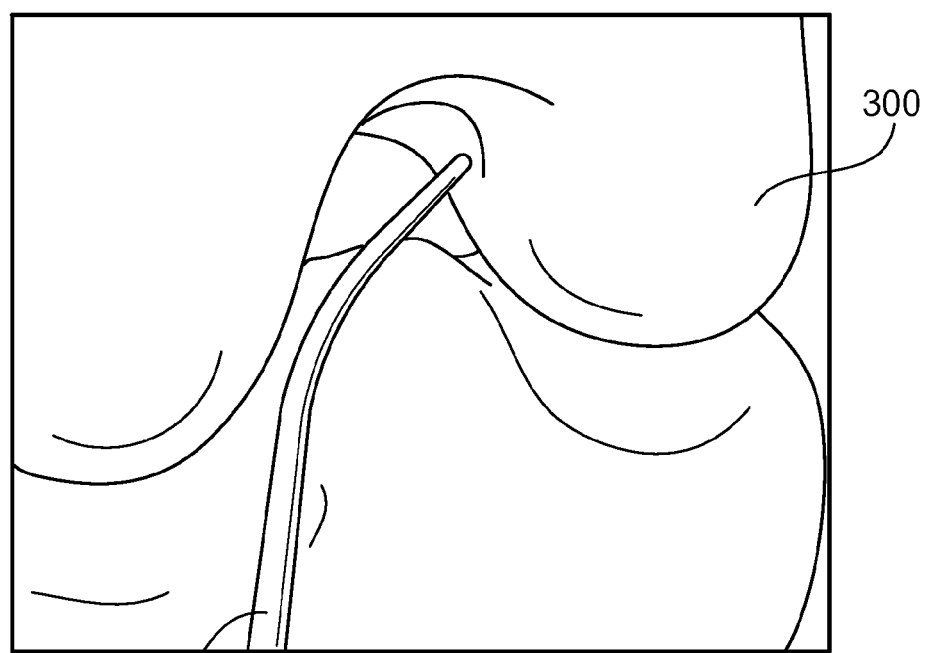

FIGS. 3A-3D illustrate a process for drilling a femoral tunnel 306 in a femur 300 via, for example, an anteromedial portal (not shown). The diameter of the femoral tunnel can be 9 mm and is larger than the largest diameter found along the hook portion 102. Referring to FIG. 3A, with the patient's knee bent to approximately 90 degrees, a curved endoscopic femoral guide 302 is introduced through the anteromedial portal. With the femoral guide 302 in position, the guide wire 200 (which may also be referred to as a drill tip passing pin) is inserted through the femoral guide 302 and advanced through the femur 300 (as best seen in FIGS. 3A-3B) and, in some cases, through the skin. Due to axial misalignment between an entry point into the anteromedial portal and a first femoral opening 308, the guide wire 200 is curved beyond 40 degrees in most cases. At this point in the process, the femoral guide 302 is removed, leaving the guide wire 200 in place.

Figure 3C:
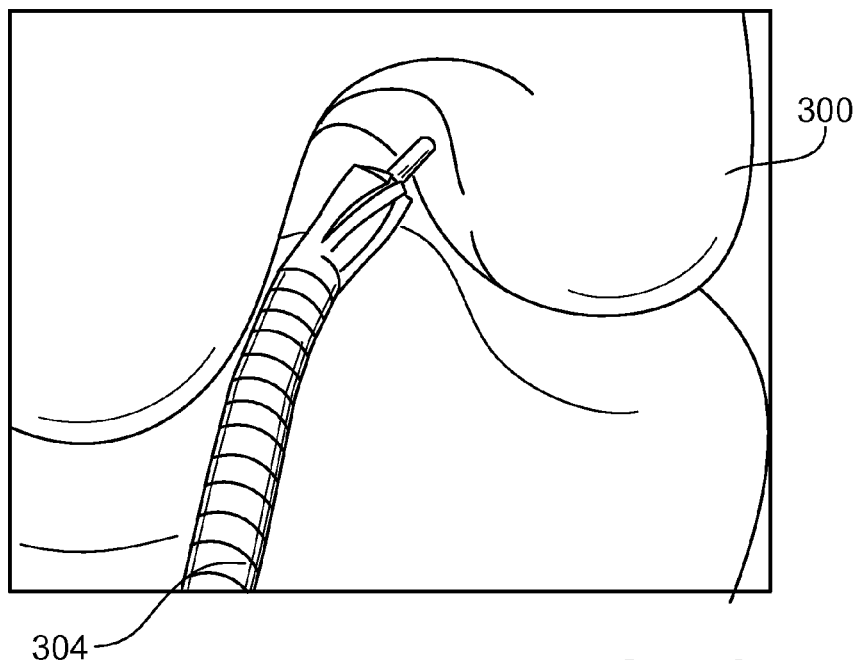
Figure 3D:
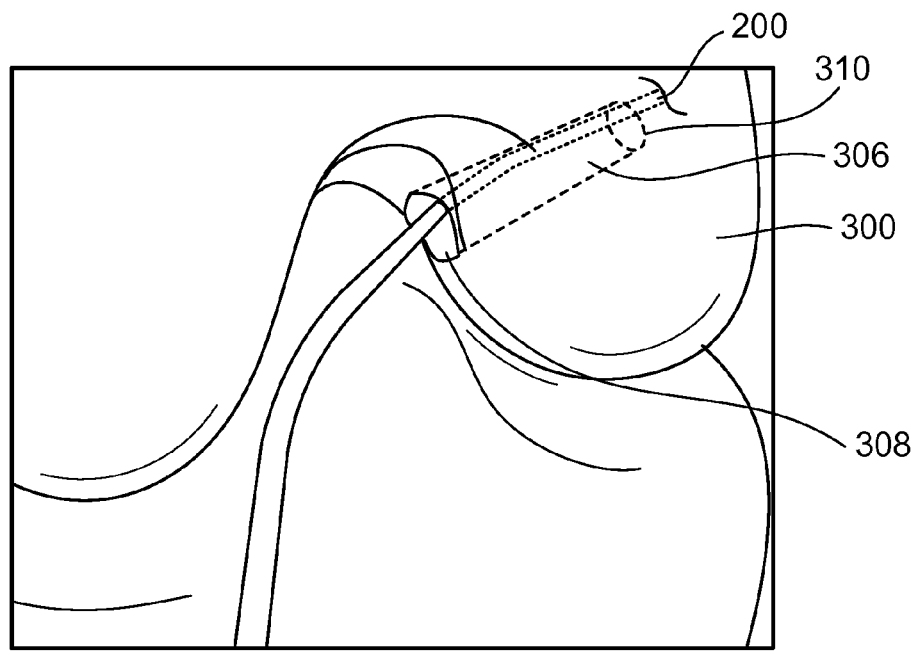

Referring to FIGS. 3C-3D, a flexible cannulated drill 304 is inserted over the guide wire 200 and advanced until the desired depth of the femoral tunnel 306 is achieved. The shape of the resulting femoral tunnel 306 follows the trajectory of the guide wire 200 and is generally straight. Additionally, the femoral tunnel 306 terminates in a second femoral opening 310 on the opposite side of the femur 300. The guide wire 200 may or may not extend beyond the second femoral opening 310.

After drilling the femoral tunnel 306 and removing the flexible cannulated drill 304, as shown in FIG. 3D, the guide wire 200 will try to straighten out by springing back, in the direction of its outer curvature 204, to its initial shape. This will result in a convex side of the flexible depth probe 100 coming in contact with an interior wall of the bone tunnel 306. In some cases, the convex side of the probe 100 may come in contact with the interior wall of the bone tunnel 306 regardless of the shape of the guide wire 200 within the femoral tunnel 306.

Referring to FIGS. 4A-4F, the flexible depth probe 100 is used to determine the length of the femoral tunnel 306. In some cases, the guide wire 200 remains in place following the drilling steps outlined in FIGS. 3A-3D. Alternatively, the guide wire 200 may be replaced with another guide wire or repositioned within the bone tunnel prior to the depth determining step. Due to axial misalignment between the anteromedial portal, where the guide wire 200 first enters the patient's body, and the first femoral opening 308, where the guide wire 200 first enters the femur 300, the guide wire 200 can be curved beyond 40 degrees.

Figure 4A:
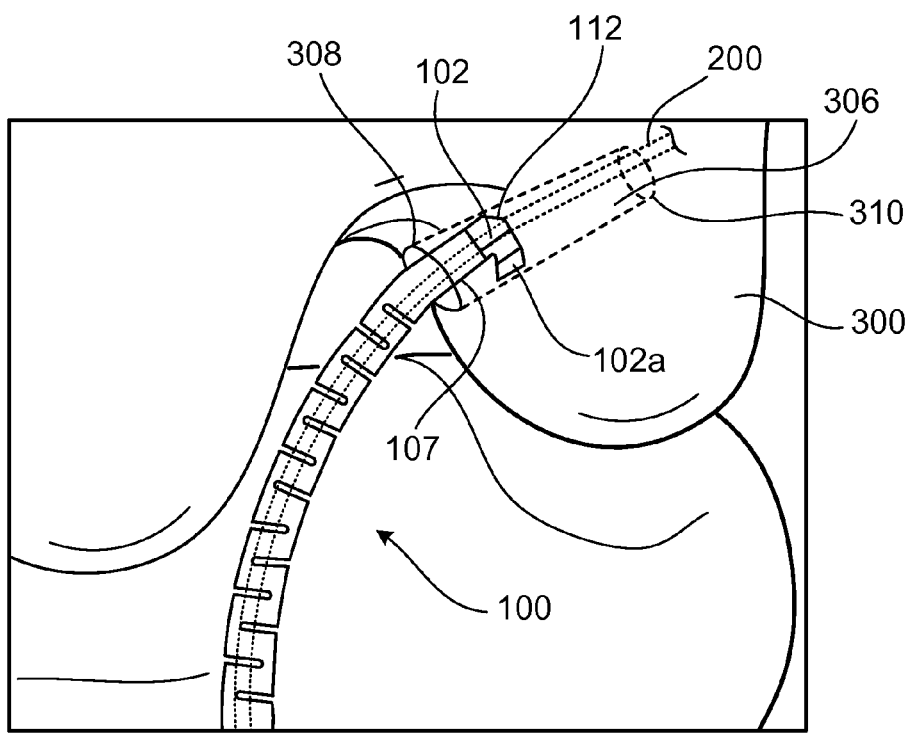
FIGS. 4A-4F illustrate a procedure using the flexible depth probe to determine the depth or length of the femoral tunnel.
Figure 4B:
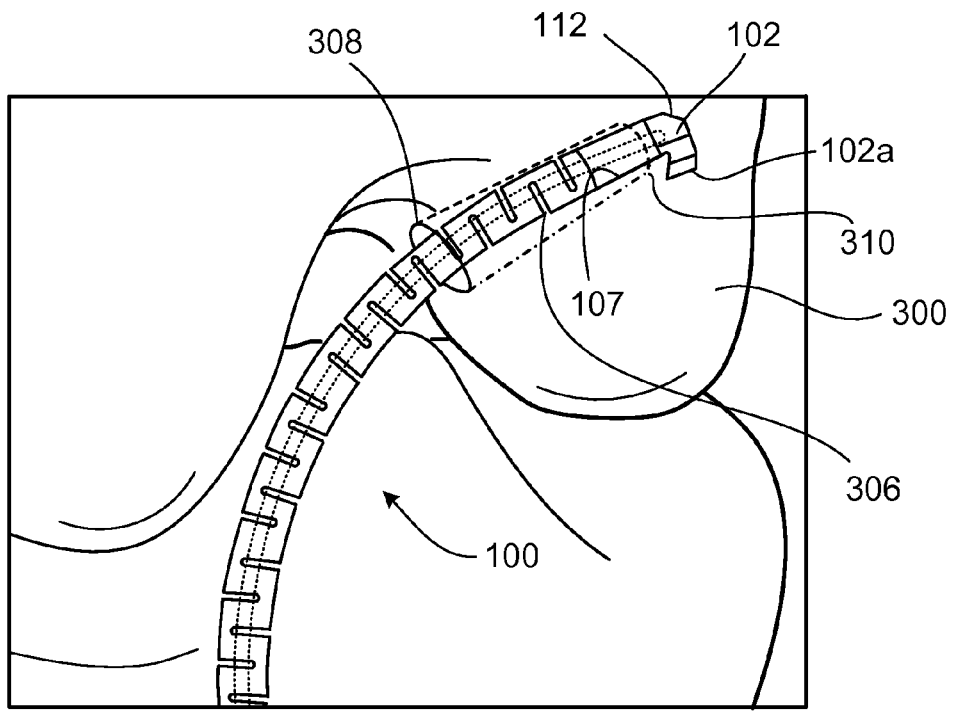
Figure 4C:
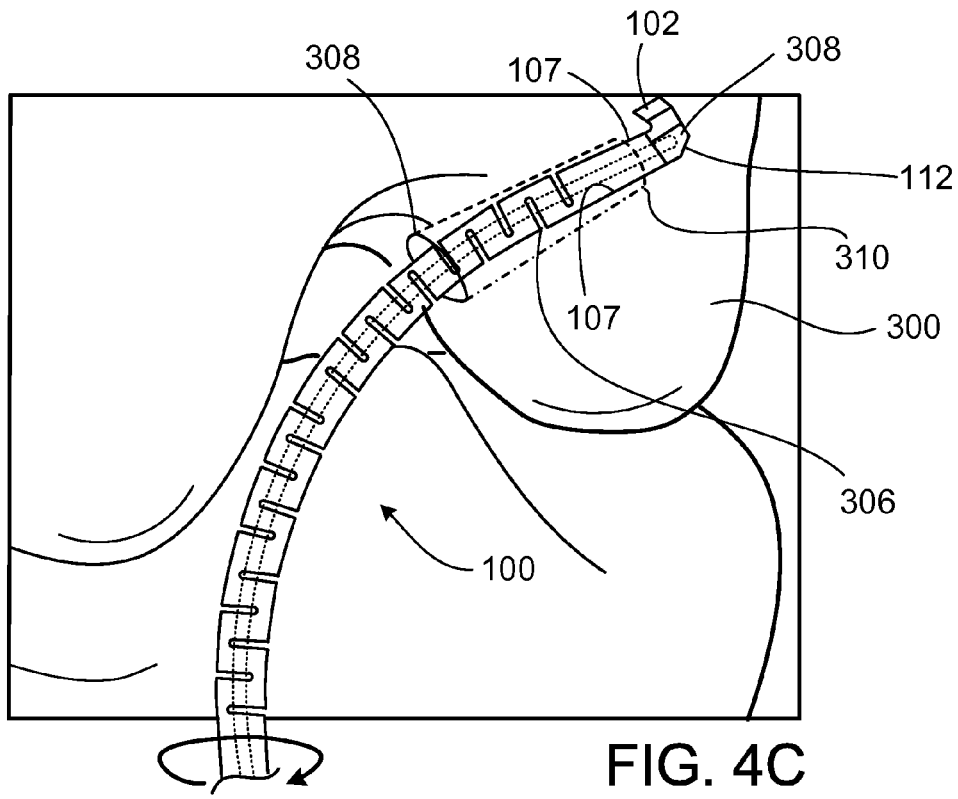
Figure 4D:
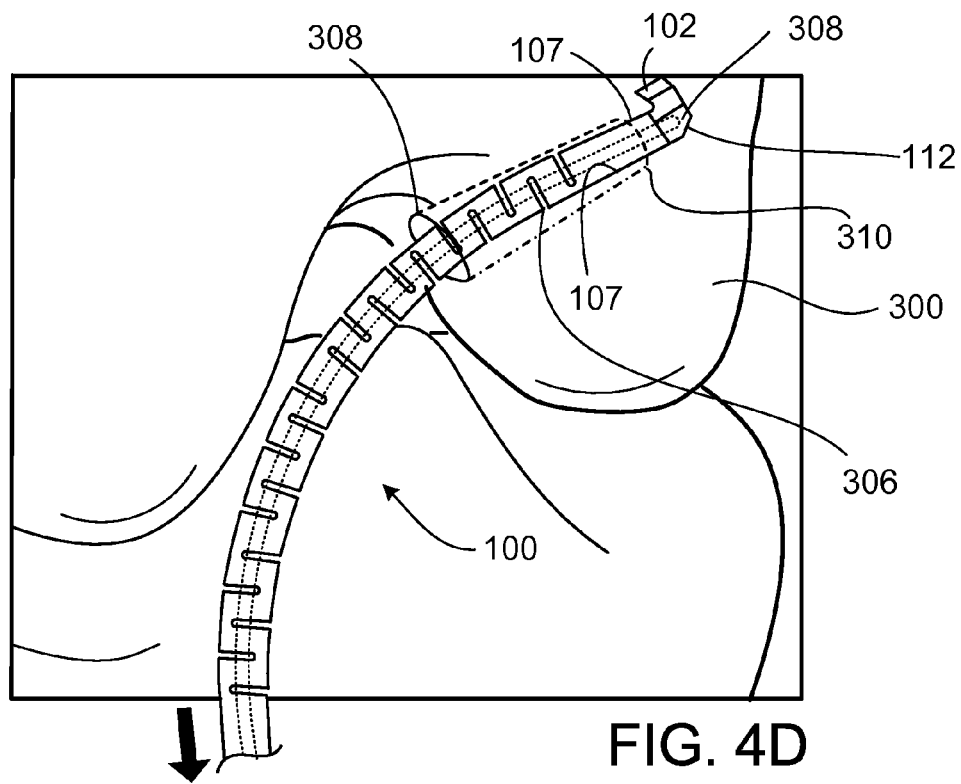
Figure 4E:
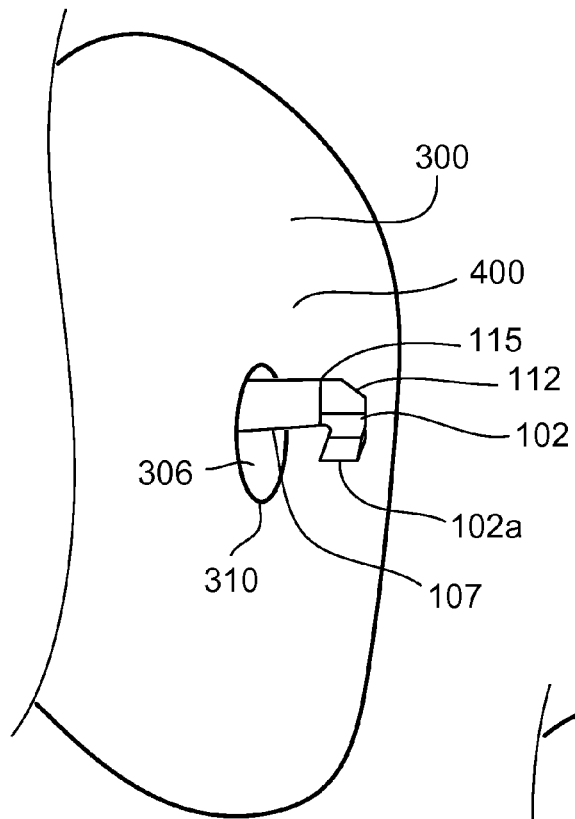
Figure 4F:
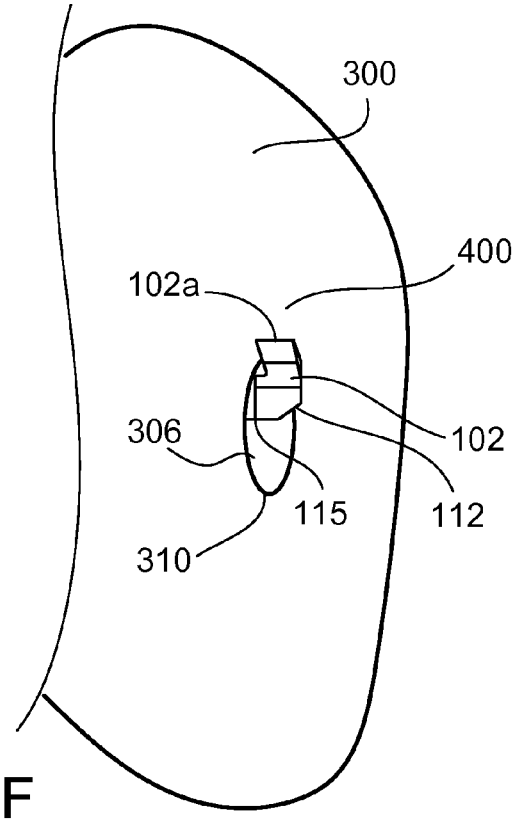

As shown in FIG. 4A, the flexible depth probe 100 is threaded over the guide wire 200 and advanced into the femoral tunnel 306 through the first femoral opening 308. By observing the orientation indicator 120, which may be inside or outside of the patient's body, the rotational orientation of the flexible depth probe 100 can be controlled such that the tip 102a of the hook portion 102 substantially faces the inner curvature 202 of the guide wire 200. Due to the tendency of the guide wire 200 and/or the flexible depth probe 100 to straighten out while in a curved state, the probe 100 will tend to push out towards the direction of the outer curvature 204 and make contact with the interior wall of the femoral tunnel 306. Because of the chamfer 112, the hook portion 102 is able to pass through the first femoral opening 308 without getting stuck and is further able to slide smoothly within the femoral tunnel 306 without snagging on or damaging the interior wall of the femoral tunnel 306. Additionally, because the diameter of the femoral tunnel is larger than the largest diameter found along the hook portion 102, the tip 102a of the hook portion 102 will not come in contact with the interior wall of the femoral tunnel 306. As shown in FIG. 4B, the flexible depth probe 100 is advanced until the hook portion 102 comes out of the femoral tunnel 306 through the second femoral opening 310.

FIGS. 4C-4F illustrate the process by which the tip 102a latches on to the cortical surface of the bone 400. After the hook portion 102 is advanced past the second femoral opening 310, the proximal end 118 of the flexible depth probe 100 is rotated by approximately 180 degrees around the guide wire 200, as indicated by arrow D in FIG. 4C. As a result, the hook portion 102 rotates approximately 180 degrees about the guide wire 200, and the tip 102a substantially faces the outer curvature 204 of the guide wire 200. Due to the tendency of the guide wire 200 and/or the flexible depth probe 100 to straighten out while in a curved state, the probe 100 will tend to push out towards the direction of the outer curvature 204 and make contact with the interior wall of the femoral tunnel 306. Because of the chamfer 107, the rotation of the flexible depth probe 100 may cause the hook portion 102 to move radially outwards in the direction of the outer curvature 204. This outward movement can provide a more secure engagement of the hook portion 102 to the cortical surface of the bone 400 by maximizing the amount of cortical surface 400 that is engaged by the tip 102a. Once the tip 102a substantially faces the outer curvature 204 of the guide wire 200, the proximal end 118 is retracted in the direction indicated by arrow E in FIG. 4D. This pulling action causes the tip 102a to engage or latch onto the cortical surface of the bone 400. Once the cortical surface of the bone 400 has been engaged by the hook portion 102, the distance between the interface region 115 and a marking 114 adjacent the first femoral opening 308 indicates the length of the femoral tunnel 306.

The above-mentioned features of the flexible depth probe 100 may enable easy removal of the probe 100 from the femoral tunnel 306 after a length has been determined, for example, by reversing the order of steps indicated in FIGS. 4A-4D. The hook portion 102 is disengaged from the cortical surface of the bone 400, for example, by pushing the proximal end 118 of the probe 100 in a direction opposite the direction indicated by arrow E. Once the hook portion 102 has been disengaged from the cortical surface 400, rotating the proximal end 118 of the probe 100 by approximately 180 degrees results in the hook portion 102 rotating by approximately 180 degrees and substantially facing the inner curvature 202 of the guide wire 200. Because of the tendency of the guide wire 200 to straighten out, the convex side of the probe 100 will push against the inner wall of the femoral tunnel 306. At this point in the process, the proximal end 118 of the probe 100 is pulled until the hook portion 102 of the probe 100, moving along the guide wire 200, passes sequentially through the second femoral opening 310, the femoral tunnel 306, the first femoral opening 308, and eventually out of the patient's body. Since the diameter of the femoral tunnel 306 is larger than the largest diameter of the hook portion 102, the tip 102a of the hook portion 102 will not snag on or damage the interior wall of the femoral tunnel 306.

While this document contains many specific implementation details, these should not be construed as limitations on the scope of any implementations or of what may be claimed, but rather as descriptions of features specific to particular implementations of particular implementations. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

The invention claimed is:

1. A measurement instrument comprising:
   a flexible shaft portion having a proximal end and a distal end, the flexible shaft portion including measurement markings along an outer surface of the flexible shaft portion; and
   a hook portion at the distal end of the flexible shaft portion;
   wherein the flexible shaft portion and the hook portion define a lumen that terminates in an opening at the hook portion,
   wherein the flexible shaft portion includes multiple, spaced apart voids along a length of the flexible shaft portion, the voids configured to provide the flexible shaft portion with flexibility,
   wherein the hook portion includes a tip extending radially outward beyond an outer diameter surface of the flexible shaft portion and a terminal end of the hook portion furthest from the flexible shaft portion angled relative to the tip in a direction back towards the proximal end of the shaft,
   wherein the tip and terminal end are substantially coplanar with respect to a plane parallel to a longitudinal axis of the shaft, and
   wherein a portion of an inner engagement surface of the hook extends back toward a proximal portion of the shaft at an acute angle relative to the shaft.

2. The instrument of claim 1, wherein the hook portion includes a first chamfer cutaway, the first chamfer cutaway disposed on a surface of the flexible shaft portion opposite the tip; and wherein the hook portion includes a second chamfer cutaway on the tip opposite the first chamfer cutaway.

3. The instrument of claim 1 further comprising a chamfered connecting portion connecting the hook portion and the flexible shaft portion, the chamfered connecting portion also defining a lumen.

4. The instrument of claim 3 wherein the chamfered connecting portion includes a chamfer along a tip-facing side of the chamfered connecting portion.

5. The instrument of claim 3, wherein the flexible shaft portion includes an orientation marking indicating a rotational orientation of the flexible shaft portion, the orientation marking aligning with the chamfered connecting portion.

6. The instrument of claim 1 wherein the voids are configured to provide the flexible shaft portion with flexibility sufficient to allow the flexible shaft portion to flex at least 40 degrees without damage.

7. The instrument of claim 1, wherein the multiple spaced apart voids are slices cut into alternating sides of the shaft portion.

8. The instrument of claim 7, wherein the multiple spaced apart voids includes a first void and a second void disposed on a particular side of the shaft portion;
   wherein the markings are measurement marking including a first measurement marking and a second measurement marking; and
   wherein the first measurement marking is disposed on the side of the shaft between the first void and the second void.

9. The instrument of claim 1, wherein the shaft includes an orientation marking indicating a rotation orientation of the shaft.

10. The instrument of claim 1, wherein the angling of the terminal end of the hook portion relative to the tip defines a cavity.

11. The instrument of claim 10, wherein the hook portion includes a chamfered cutaway on a surface of the flexible shaft portion opposite the tip, the chamfered cutaway on the surface of the flexible shaft portion opposite the tip exposing the lumen on a side wall along an axial length of the flexible shaft portion.

12. The instrument of claim 11, wherein the cavity includes a chamfered connecting portion connecting the hook portion and the flexible shaft portion, the chamfered connection portion in the cavity providing an opening to the lumen.

13. The instrument of claim 12, wherein the flexible shaft portion includes multiple spaced-apart voids along a length of the flexible shaft portion, the multiple spaced-apart voids configured to provide the flexible shaft portion with flexibility.

14. The instrument of claim 13, wherein the proximal end of the flexible shaft portion includes an orientation indicator that indicates a rotational orientation of the tip disposed on the hook portion.

15. The instrument of claim 14, wherein the proximal end of the flexible shaft portion includes an outer circumferential surface region on which the orientation indicator resides.

16. A measurement instrument comprising:
   a flexible shaft portion having a proximal end and a distal end, the flexible shaft portion including measurement markings along an outer surface of the flexible shaft portion;
   a hook portion at the distal end of the flexible shaft portion;

wherein the flexible shaft portion and the hook portion define a lumen that terminates in an opening at the hook portion;

wherein the hook portion includes a tip, the tip extending radially outward beyond an outer diameter surface of the flexible shaft portion, a terminal end of the hook portion furthest from the flexible shaft portion angled in a direction back towards the proximal end to form a cavity;

wherein the hook portion includes a chamfered cutaway on a surface of the flexible shaft portion opposite the tip, the chamfered cutaway on the surface of the flexible shaft portion opposite the tip exposing the lumen on a side wall along an axial length of the flexible shaft portion;

wherein the cavity includes a chamfered connecting portion connecting the hook portion and the flexible shaft portion, the chamfered connection portion in the cavity providing an opening to the lumen; and wherein the proximal end of the flexible shaft portion includes an orientation indicator that indicates a rotational orientation of the hook portion disposed on the distal end of the flexible shaft portion.

17. A method of determining a length of a bone tunnel in a respective bone using a measurement instrument that includes a flexible shaft portion and a hook portion at a distal end of the flexible shaft portion, the method comprising:

placing the instrument into a curved guide wire that passes through the bone tunnel;

moving the flexible shaft portion of the instrument along the curved guide wire until the hook portion passes through a first opening of the bone tunnel, through the bone tunnel, and out a second opening of the bone tunnel;

orienting the flexible shaft portion of the instrument such that a tip of the hook portion faces an outer curvature of the guide wire;

maintaining the orientation of the flexible shaft portion with the tip of the hook portion facing the outer curvature of the guide wire while retracing the instrument until the tip of the hook portion facing the outer curvature of the guide wire engages a cortical surface of the respective bone; and determining the length of the bone tunnel based on measurement markings along an outer surface of the flexible shaft portion.

18. The method of claim 17 wherein the flexible shaft portion and the hook portion define a lumen that terminates in an opening at the hook portion; and wherein placing the instrument into the curved guide wire includes threading the opening and lumen over the guide wire.

19. The method of claim 17 wherein the instrument is oriented such that the tip of the hook portion faces an inner curvature of the guide wire while the hook portion passes through the first opening of the bone tunnel, through the bone tunnel, and out the second opening of the bone tunnel.

20. The method of claim 17 wherein orienting the instrument such that the tip of the hook portion faces the outer curvature of the guide wire includes rotating the instrument around the guide wire until the tip of the hook portion faces the outer curvature of the guide wire.

21. The method of claim 17 further comprising:

disengaging the hook portion from the cortical surface;

orienting the instrument such that the tip of the hook portion faces an inner curvature of the guide wire; and moving the instrument along the curved guide wire until the hook portion passes through the second opening of the bone tunnel, through the bone tunnel, and out the first opening of the bone tunnel.

22. The method of claim 17 further comprising determining an orientation of the hook portion based on the orientation indicator that indicates the orientation of the hook portion, the orientation indicator being located at a proximal end of the flexible shaft portion.

23. The method as in claim 17, wherein the flexible shaft portion has a tendency to straighten out, facilitating engagement of the tip of the hook portion with the cortical surface of the respective bone.

24. The method as in claim 17, wherein the bone tunnel has a larger diameter than a diameter of the hook portion disposed at the distal end of the flexible shaft portion.

25. The method as in claim 23 further comprising:

orientating the flexible shaft portion such that a tip of the hook portion faces an inner curvature of the guide wire to disengage the tip of the hook portion from the cortical surface of the bone; and retracting the flexible shaft portion from the bone tunnel.

* * * * *